(12) United States Patent
Bianchi et al.

(10) Patent No.: US 7,759,529 B2
(45) Date of Patent: Jul. 20, 2010

(54) CONTINUOUS PROCESS FOR THE PREPARATION OF PHENOL FROM BENZENE IN A FIXED BED REACTOR

(75) Inventors: Daniele Bianchi, Arese-Milano (IT); Rossella Bortolo, Novara (IT); Chiara Busto, Trecate-Novara (IT); Carla Lazzari, Cornaredo-Milano (IT)

(73) Assignee: Polimeri Europa S.p.A., Brindisi (IT)

( * ) Notice: Subject to any disclaimer, the term of this patent is extended or adjusted under 35 U.S.C. 154(b) by 126 days.

(21) Appl. No.: 11/575,579

(22) PCT Filed: Oct. 26, 2005

(86) PCT No.: PCT/EP2005/011575

§ 371 (c)(1),
(2), (4) Date: Mar. 20, 2007

(87) PCT Pub. No.: WO2006/050827

PCT Pub. Date: May 18, 2006

(65) Prior Publication Data

US 2007/0255078 A1  Nov. 1, 2007

(30) Foreign Application Priority Data

Nov. 12, 2004  (IT) ................. MI2004A2169

(51) Int. Cl.
*C07C 29/14* (2006.01)
(52) U.S. Cl. .................................... 568/800
(58) Field of Classification Search .............. None
See application file for complete search history.

(56) References Cited

U.S. PATENT DOCUMENTS

| | | | | |
|---|---|---|---|---|
| 4,147,726 A * | 4/1979 | Wu | ............... | 568/342 |
| 5,233,097 A * | 8/1993 | Nemeth et al. | ............... | 568/803 |
| 6,133,487 A * | 10/2000 | Ungarelli et al. | ............ | 568/803 |
| 6,156,939 A | 12/2000 | Vignola et al. | | |
| 7,038,093 B2 | 5/2006 | Bianchi et al. | | |
| 2001/0021369 A1* | 9/2001 | Lin et al. | ................... | 423/713 |
| 2002/0048536 A1* | 4/2002 | Bergh et al. | ................ | 422/130 |

FOREIGN PATENT DOCUMENTS

| | | |
|---|---|---|
| EP | 0 919 531 | 6/1999 |
| EP | 0 958 861 | 11/1999 |
| EP | 1 424 320 | 6/2004 |
| WO | 03 042146 | 5/2003 |
| WO | WO 03/042146 A1 * | 5/2003 |
| WO | WO 03042146 * | 5/2003 |

\* cited by examiner

*Primary Examiner*—Jafar Parsa
*Assistant Examiner*—Chukwuma O Nwaonicha
(74) *Attorney, Agent, or Firm*—Oblon, Spivak, McClelland, Maier & Neustadt, L.L.P.

(57) ABSTRACT

The invention relates to a continuous process for the preparation of phenol by means of the direct oxidation of benzene with hydrogen peroxide in the presence of a catalyst based on titanium silicalite TS-1 comprising: (a) running the process in a fixed bed reactor containing the catalyst based on TS-1 at a temperature ranging from 80-120° C. and at a pressure ranging from 3-15 atm; (b) feeding to the reactor a stream containing $H_2O_2$, benzene, sulfolane and water in a single or double phase, wherein the quantities of the single components are within the range of 0.2-6, 15-60, 30-80, 0.5-30 parts by weight, respectively, for every 100 units fed and whose total flow rate is calculated so that the residence time in the reactor (defined as the ratio between the quantity of catalyst by weight and the feeding flow rate) ranges from 0.3 to 2 min; (c) recovery of the products, by-products and solvent from the liquid stream leaving the reactor.

9 Claims, 1 Drawing Sheet

CONTINUOUS PROCESS FOR THE PREPARATION OF PHENOL FROM BENZENE IN A FIXED BED REACTOR

BACKGROUND OF THE INVENTION

The invention relates to a continuous process for the preparation of phenol by the direct oxidation of benzene with hydrogen peroxide, carried out in a fixed bed reactor.

More specifically, the invention relates to a process for the preparation of phenol wherein the oxidation reaction is carried out in the presence of a catalyst based on titanium silicalite and under particular operative conditions.

The invention also relates to a process for the activation of the catalyst based on titanium silicalite TS-1.

Phenol is an industrial intermediate of great importance, which is widely used in the production of polycarbonates or other phenolic resins.

Phenol is currently produced according to the "Hock process", which contemplates the alkylation of benzene to cumene and subsequent oxidation of cumene to hydroperoxide, which decomposes to phenol and acetone.

Various processes are known in the art for the preparation of phenol, which are based on the direct oxidation of benzene with hydrogen peroxide, in the presence of suitable catalytic systems.

A process is known, for example, which is carried out in the presence of a catalyst based on titanium silicalite and in an organic solvent capable of enhancing the contact between the organic substrate and hydrogen peroxide.

The conversion and selectivity of processes for the preparation of phenol by direct oxidation can be improved by operating in the presence of specific solvents, such as sulfolane, for example (EP A 919531).

In this case, the process is carried out in a batch-type reactor operating in a two-phase reaction system consisting of the solid catalyst and an organic phase comprising sulfolane/water/benzene in such a ratio as to make the reaction mixture homogeneous.

Improvements in the productivity of processes for the production of phenol can also be obtained by activation of the catalyst with hydrogen peroxide and fluorine ions, as described in European patent application EP A 958861.

Further improvements can be obtained by operating in a three-phase reaction system consisting of a solid catalyst, an aqueous phase and an organic phase comprising the aromatic compound and the solvent, as described in patent application PCT/EP02/12169.

BRIEF SUMMARY OF THE INVENTION

The processes for the preparation of phenol by the direct oxidation of benzene described in the known art are generally carried out in CSTR-type reactors in which the catalyst based on titanium silicalite is kept in suspension in the form of a fine powder.

In these processes, the separation of the reaction effluent from the catalyst can only be effectively carried out by filtration inside the reactor.

This operation, however, cannot be effected in the processes of the known art because, as a result of the low concentrations of the products, the filtrating surface necessary would be too high.

The only possible technological solution consequently consists in effecting the filtration outside the CSTR reactors. This, however, is technologically complex due to the necessity of using both additional equipment and abrasion-resistant materials and also of maintaining the efficiency of the filters.

A process has now been found which allows the direct synthesis of phenol from benzene with high conversions and productivities and at the same time eliminating the problems due to filtration.

In practice, the invention envisages that the process be carried out in continuous in a fixed bed reactor, operating under particular operating conditions and according to two different procedures: in homogeneous liquid phase or with two liquid phases using, in both cases, sulfolane as solvent.

In accordance with this, the object of the present invention relates to a continuous process for the preparation of phenol by means of the direct oxidation of benzene with hydrogen peroxide in the presence of a catalyst based on titanium silicalite TS-1 comprising:

(a) running the process in a fixed bed reactor containing the catalyst based on TS-1 at a temperature ranging from 80-120° C. and at a pressure ranging from 3-15 atm;

(b) feeding to the reactor a stream containing $H_2O_2$, benzene, sulfolane and water in a single or double phase, wherein the quantities of the single components are within the range of 0.2-6, 15-60, 30-80, 0.5-30 parts by weight, respectively, for every 100 units fed and whose total flow rate is calculated so that the residence time in the reactor ranges from 0.3 to 2 min (wherein the residence time is the ratio between the weight quantity of catalyst and the feeding flow rate);

(c) recovery of the products, by-products and solvent from the liquid stream leaving the reactor.

The process of the present invention allows different advantages to be obtained:

it considerably simplifies the operations involved in oxidation processes of aromatic substrates, as filtration is no longer required and it also avoids recycling of part of the liquid reaction effluent;

it reduces the investment costs for the production of the plant;

it makes the process more versatile as it is also possible to operate with two liquid phases (three-phase system).

The process of the invention can be effectively carried out in continuous and operating with several reactors.

In this case, it has been found that it is possible to improve the selectivity, by subdividing the feeding of hydrogen peroxide in equal parts between the various reactors.

BRIEF DESCRIPTION OF THE DRAWING

The FIGURE shows a preferred embodiment of the invention.

Figure 1:
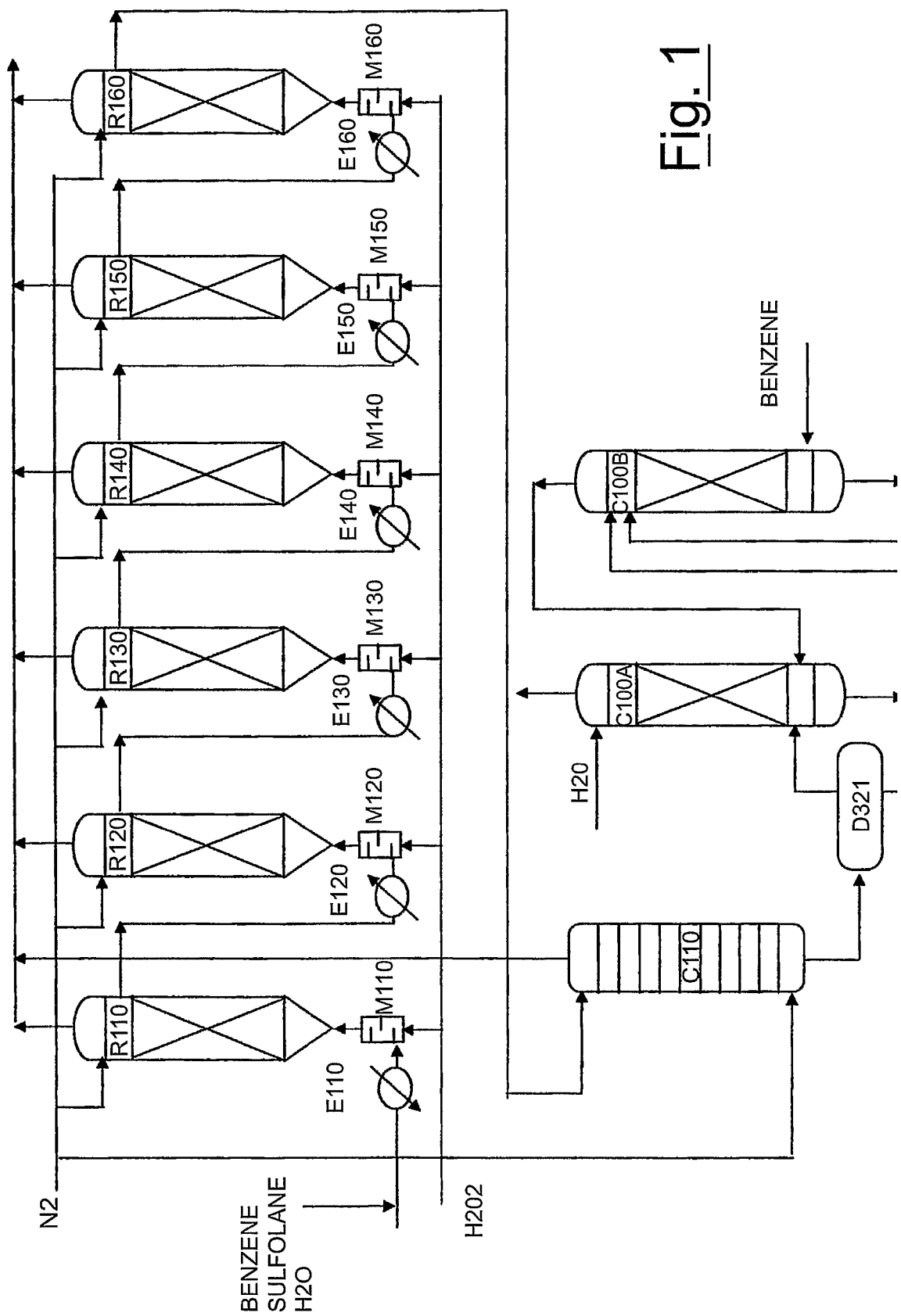

DETAILED DESCRIPTION OF THE INVENTION.

The process of the invention is carried out in a fixed bed reactor (plug-flow) charged with the catalyst based on titanium silicalite.

The catalysts of the invention are titanium silicalites with an MFI structure and having the general formula $xTiO_2 \cdot (1-x)SiO_2$ with x ranging from 0.0001 and 0.04.

The structural characteristics of these catalysts as also their preparation method are described in the patents U.S. Pat. Nos. 4,410,501, 4,954,653, 4,701,428, EP A906784.

The catalysts of the invention are used in extruded form by formulating the titanium silicalite with an inert ligand, such as silica, according to the techniques known to experts in the field.

Examples of these formulations can be found in patents U.S. Pat. Nos. 6,491,861, 6,551,546, US 2003/0078160, US 2003/0130116.

The reaction for the production of phenol by the direct oxidation of benzene with $H_2O_2$, can be carried out according to two different procedures: in homogeneous liquid phase (double phase system) or with two liquid phases (triple phase system) in both cases using sulfolane as solvent.

In the process for the production of phenol, the feeding ratio between $H_2O_2$, benzene, sulfolane and water lead to the presence of a single liquid phase or two immiscible phases.

When operating in a single liquid phase, the feeding quantities of $H_2O_2$, benzene, sulfolane and water generally range from 0.2-4, 20-60, 40-80, 0.5-5 parts by weight, respectively, per 100 units fed; whereas when operating in the presence of two immiscible phases, the quantities range from 0.3-6, 15-50, 30-70, 10-30.

In both cases, the total flow-rate is calculated so that the residence time ranges from 0.3 to 2 min.

The oxidation of benzene to phenol with hydrogen peroxide is preferably effected in a system consisting of a series of fixed bed plug-flow reactors (from a minimum of two to a maximum of 10 reactors).

Each reactor consists of a single catalyst bed with or without an outer heating jacket.

In this latter case, the reactors operate adiabaticcally and the activation treatment of the catalyst is effected in a specific apparatus.

The scheme of the reaction section shown in FIG. 1 considers, in particular, six tubular reactors called R110, . . . , R160. The liquid flows indicated are intended as the homogeneous liquid phase or the sum of the two immiscible phases, according to the cases.

All the benzene and sulfolane necessary for the reaction are mixed (M110) and sent to the first reactor (R110).

The hydrogen peroxide in aqueous solution, on the other hand, is subdivided into equal parts and added (in M110-M160) to the main flow before each reactor in order to keep the concentration low and consequently limit its decomposition to oxygen.

Each reactor completely uses up the quantity of hydrogen peroxide fed.

By subdividing the hydrogen peroxide among various reactors, the concentration of phenol formed in the first reactors is also kept low; in this way, it is possible to limit reactions leading to the formation of by-products (catechol and hydroquinone) more effectively than when operating with a lower number of reactors.

The quantity of reagents fed to the various reactors varies according to whether the procedure is effected in single or double phase.

Typically, when operating in single phase, the quantities of the components of the feeding stream (expressed in parts by weight per 100 units fed) range from 0.2-4 for the hydrogen peroxide, 20-60 for the benzene, 40-80 for the sulfolane, 0.5-5 for the water and preferably 0.2-4 for the hydrogen peroxide, 30-50 for the benzene, 45-70 for the sulfolane, 0.5-5 for the water.

Operating in double phase, on the other hand, the quantities of the components of the feeding stream (expressed in parts by weight per 100 units fed) range from 0.3-6 for the hydrogen peroxide, 15-50 for the benzene, 30-70 for the sulfolane, 10-30 for the water and preferably 0.3-5 for the hydrogen peroxide, 20-40 for the benzene, 35-60 for the sulfolane, 10-30 for the water.

Nitrogen is sent to the top of each reactor to keep the vapours outside the explosive limit.

The reactors can operate either under adiabatic conditions or in the presence of thermostat-regulation, with a temperature range of 80-120° C. and a pressure of 3-15 atm, preferably 90-110° C. and 5-7 atm.

A heat exchanger (M110, . . . , M160) is present between one reactor and another to lower the temperature of the outgoing flow before feeding it to the subsequent reactor.

In the case of adiabatic reactors, the absence of thermal exchange (in the reactors) makes them particularly simple from the point of view of construction.

The total feeding flow-rate is calculated so that the residence time in the reactor ranges from 0.3 to 2 min.

By operating in coherence with the invention described so far, 100% conversions of $H_2O_2$ are obtained, with a selectivity of benzene in the order of 85-92%.

Furthermore, by operating in double phase, the reaction rate is increased with respect to the homogeneous phase, which allows lower quantities of catalyst and smaller reactors to be used and also limiting the temperature to lower values.

The double phase allows the selectivity of benzene to be kept unaltered as also the quantity of catechol and hydroquinone formed.

The catalytic properties of the catalyst used in the oxidation of benzene can be improved by means of an activation treatment with fluorides and hydrogen peroxide.

The treatment can be effected on the powder, before extrusion, in a batch process, the treatment being followed by a series of washings with water and filtrations (as described in patent EP 958861).

It has now been found that the activation process can be carried out in continuous directly in the column in which the synthesis reaction takes place: in this way, the treatment is simpler and more easy to apply on an industrial scale.

The activation process of the present invention envisages that the quantities of catalyst to be treated and reagents be selected so as to have a fluorine/titanium molar ratio ranging from 0.5 to 3.0, preferably 2.5 and an $H_2O_2$/titanium molar ratio ranging from 3.0 to 15, preferably 11.

The catalyst can be used as such or closely mixed with an inert material, of similar dimensions, in a quantity equal to the weight of the catalyst itself.

The inert material can be selected from quartz, corundum, ceramic material, glass, extruded silica, preferably quartz.

The catalyst or its mixture with the inert material is charged into the reactor which is subsequently brought to temperatures ranging from 20 to 120° C., preferably 80° C., and fed with an aqueous solution of ammonium acid fluoride ($NH_4HF_2$) and hydrogen peroxide.

The feeding time ranges from 2 to 6 hours, preferably 4 hours.

The feeding solution contains ammonium acid fluoride in a concentration ranging from 0.1% to 1% by weight, preferably 0.25%, and hydrogen peroxide in a concentration ranging from 3% to 10% by weight, preferably 4.8%. At the end of the reaction, the reactor is fed with water to eliminate the reagent residues and then emptied of the liquid and the catalyst undergoes a calcination or drying treatment.

The liquid effluent leaving the reactor at the end of the reaction containing the products and by-products as well as the solvent to be recovered for re-use, must be subjected to the purification section.

The purification of the products and recovery of the solvent can be effected by means of the process described in patent EP 3076502.

This process, however, has the disadvantage that the solution coming from the reactor and sent to the distillation section contains a high quantity of water and sulfolane whose presence makes the production of pure phenol difficult.

A process has now been found for the recovery of the products and solvent which allows the quantity of water and sulfolane sent to distillation to be reduced, consequently obtaining more efficient and economical distillation operations.

In practice, the process of the invention envisages that the two-phase liquid stream leaving the reactors be subjected to a liquid-liquid extraction using water and benzene as extraction solvents.

The water is fed to the head of the column and has the function of prevalently extracting the sulfolane, whereas the benzene, which is fed to the bottom of the column, has the function of prevalently extracting the phenol.

The biphenols and other by-products are divided into the two streams.

The organic stream, enriched in benzene and phenol is sent to distillation whereas the aqueous stream, enriched in water and sulfolane is sent directly for salification to recover the biphenols.

More specifically, the reaction mixture, containing benzene, water, phenol, sulfolane and reaction by-products (biphenols), is sent to one or more extraction columns to which benzene and water are also sent. The water (fresh or recycled from other equipment) is fed from above, the reaction mixture is fed to an intermediate point, whereas the benzene (fresh or recycled from other equipment) is sent from below. A light organic phase, richer in benzene and phenol and with less sulfolane and water with respect to the mixture coming from the reaction, leaves the head of the column; a heavy aqueous phase richer in water and sulfolane and poorer in benzene and phenol with respect to the mixture coming from the reaction leaves the bottom of the column.

The organic phase is sent to the distillation section, whereas the aqueous phase is sent to the salification unit of biphenols.

The distillation and biphenol recovery sections have a configuration which is analogous to that described in U.S. patent Ser. No. 10/716,460, but thanks to the previous extraction section, have reduced dimensions and lower energy consumptions.

In addition to the separation and purification of the phenol, the procedure adopted allows the purified solvent containing the necessary benzene for recycling to the oxidation reactor to be obtained, as well as biphenols dissolved in water which are then retransformed into phenol by means of catalytic hydrodeoxygenation, as described in U.S. Ser. No. 10/716,460).

EXAMPLE 1

Activation of the Catalyst 7100 kg of TS1 catalyst (extruded with 15% by weight of silica) are charged into a tubular reactor, as described in Examples 2 and 3, which is brought to a temperature of 80° C.

207 kg of ammonium acid fluoride ($NH_4HF_2$) and 3944 kg of hydrogen peroxide at 30% by weight, are dissolved in 81,000 kg of distilled water, and fed to the reactor with a flow-rate of 20 m$^3$/h. At the end of the addition, the reactor is fed with 40,500 kg of water to remove the reagent residues. Finally, the reactor is emptied and the temperature is brought to 350° C. for 8 hours, under a flow of inert gas.

The catalyst thus treated is ready to be used for the synthesis of phenol, and proves to have the following composition: $SiO_2$=98.20%, $TiO_2$=1.80%.

EXAMPLE 2

Preparation of Phenol in Homogeneous Phase

The benzene and sulfolane fed to M110 are 251.1 t/h and 363.35 t/h respectively. Each of the six streams of hydrogen peroxide (at 40% by weight of water) to 3.36 t/h.

M110 mixes and E110 heats the feeds from room temperature to 100° C.

In R110 the hydrogen peroxide is completely converted to reaction products and, by operating adiabaticcally, the temperature rises from 100° C. to 112° C.

M120 mixes the effluent of the first reactor with the second quantity of hydrogen peroxide and E120 cools this stream to 100° C. As the quantities of hydrogen peroxide are comparable, the temperature increase in R120 also passes from 100° C. to 112° C.

The subsequent M130, . . . , M160 and E130, . . . , E160 have the same function as M120 and E120 and the reactors R130, . . . , R160 behave analogously to R120.

Each of the reactors contains 9,000 kg of catalyst (activated as described in example 1), and has the following dimensions: D=2.75 m, H=3.14 m.

The liquid effluent leaving the last reactor has a flow-rate of 639.8 t/h and the following composition: benzene=35.9% w, phenol=3.20% w, catechol=0.55% w, hydroquinone=0.29% w, sulfolane=56.79% w, water=3.23% w.

The overall performances obtained are:

| Conversion of $H_2O_2$ | [%] | 100 |
|---|---|---|
| Selectivity of benzene | [%] | 87.5 |
| Selectivity of $H_2O_2$ | [%] | 74.0 |
| $H_2O_2$ to $O_2$ | [%] | 5.3 |
| $H_2O_2$ to (catechol + hydroquinone) | [%] | 21.0 |

EXAMPLE 3

Preparation of Phenol in Double Phase

The benzene, water and sulfolane fed to M120 are equal to 143.19 t/h, 2,226.33 t/h and 96.36 t/h respectively. Each of the six streams of hydrogen peroxide (at 65% by weight of water) is equal to 6.12 t/h.

M110 mixes and E110 heats the feeds from room temperature to 95° C.

In R110 the hydrogen peroxide is completely converted to reaction products and, by operating adiabatically, the temperature rises from 95° C. to 108.5° C.

M120 mixes the effluent of the first reactor (biphasic mixture) with the second quantity of hydrogen peroxide and E120 cools this stream to 95° C. As the quantities of hydrogen peroxide are comparable, the temperature increase in R120 also passes from 95° C. to 108.5° C.

The subsequent M130, . . . , M160 and E130, . . . , E160 have the same function as M120 and E120 and the reactors R130, . . . , R160 behave analogously to R120.

Each of the reactors contains 7,100 kg of catalyst (activated as described in example 1), and has the following dimensions: D=2.54 m, H=2.91 m.

The liquid stream (biphasic) leaving the last reactor, has a flow-rate of 493.80 t/h and the following composition: benzene=23.73% w, phenol=4.41% w, catechol=0.54% w, hydroquinone=0.29% w, sulfolane=45.83% w, water=24.73% w.

The overall performances obtained are:

| | | |
|---|---|---|
| Conversion of $H_2O$ | [%] | 100 |
| Selectivity of benzene | [%] | 85 |
| Selectivity of $H_2O_2$ | [%] | 61.5 |
| $H_2O_2$ to $O_2$ | [%] | 16 |
| $H_2O_2$ to (catechol + hydroquinone) | [%] | 19.8 |

The invention claimed is:

1. A continuous process for the preparation of phenol by the direct oxidation of benzene with hydrogen peroxide comprising:
   activating a catalyst in a fixed bed reactor for the direct oxidation;
   feeding to the fixed bed reactor having the activated catalyst, a stream containing $H_2O_2$, benzene, sulfolane and water in a single or double phase;
   oxidizing the benzene at a temperature ranging from 80-120° C. and at a pressure ranging from 3-15 atm in the presence of the fixed catalyst; and
   recovering the products, by-products and solvent from the liquid stream leaving the reactor; wherein
   the liquid stream leaving the reactor comprises phenol, benzene, reaction by-products, sulfolane and water,
   the catalyst is represented by the formula:

$x\text{TiO}_2(1-x)\text{SiO}_2$ wherein
   x is from 0.0001 to 0.04,
   the quantities of the single components are within the range of 0.2-6, 15-60, 30-80, 0.5-30 parts by weight, respectively, for every 100 units fed, and
   a total flow rate is calculated so that a residence time in the reactor ranges from 0.3 to 2 min.

2. The process according to claim 1, wherein the temperature ranges from 90-110° C. and the pressure ranges from 5-7 atm.

3. The process according to claim 1, wherein
   the stream containing $H_2O_2$, benzene, sulfolane and water is in double phase,
   the quantities of the single components respectively range from 0.3-6, 15-50, 30-70, 10-30 parts by weight per 100 units fed and
   the total flow-rate is calculated so that the residence time in the reactor ranges from 0.3 to 2 min.

4. The process according to claim 3, wherein the quantities of the single components respectively range from 0.3-5, 20-40, 35-60, and 10-30 parts by weight per 100 units fed.

5. The process according to claim 1, wherein the fixed bed reactor comprises from two to ten fixed bed plug-flow reactors arranged in series.

6. The process according to claim 5, wherein the feeding of the hydrogen peroxide comprises subdividing the hydrogen peroxide into equal parts corresponding to the number of reactors, and adding one equal part to the stream fed to an individual reactor.

7. The process according to claim 5, wherein the residence time of the feeding stream in each reactor ranges from 0.4 to 2.0 minutes.

8. The process according to claim 1, wherein the catalyst is in extruded form.

9. The process according to claim 1, wherein the recovery of the products, by-products and solvent from the liquid stream leaving the reactor, comprises:
   sending the liquid stream leaving the reactors containing benzene, water, phenol, sulfolane and the reaction by-products to an intermediate point of one or more extraction columns;
   feeding fresh or recycled water from the top of the extraction column;
   feeding fresh or recycled benzene from the bottom of the distillation column;
   sending the light organic phase leaving the head of the distillation column, richer in benzene and phenol and poorer in sulfolane and water, to the distillation section;
   sending the heavy aqueous phase richer in water and sulfolane and poorer in benzene and phenol, to the salification section of biphenols for their recovery;
   recycling the purified sulfolane containing benzene, recovered in the distillation section, to the oxidation reactor.

* * * * *